United States Patent [19]
Growdon et al.

[11] Patent Number: 5,631,168
[45] Date of Patent: May 20, 1997

[54] ANTEMORTEM DIAGNOSTIC TEST FOR ALZHEIMER'S DISEASE

[75] Inventors: John H. Growdon, Chestnut Hill; Roger M. Nitsch; Richard J. Wurtman, both of Boston, all of Mass.

[73] Assignee: Massachusetts Institute of Technology, Cambridge, Mass.

[21] Appl. No.: 353,960

[22] Filed: Dec. 12, 1994

Related U.S. Application Data

[63] Continuation of Ser. No. 959,084, Oct. 9, 1992, abandoned.

[51] Int. Cl.$^6$ .................................................. G01N 33/92
[52] U.S. Cl. .................................................. 436/71; 435/4
[58] Field of Search .................................................. 436/71; 435/4

[56] References Cited

U.S. PATENT DOCUMENTS

| | | | |
|---|---|---|---|
| 4,874,694 | 10/1989 | Gandy et al. | 435/15 |
| 4,918,062 | 4/1990 | Lodi | 514/76 |
| 5,006,462 | 4/1991 | Gahaz | 435/7.4 |
| 5,051,410 | 9/1991 | Wurtman et al. | 514/78 |

FOREIGN PATENT DOCUMENTS

| | | |
|---|---|---|
| 0 459 454 A1 | 12/1991 | European Pat. Off. . |
| 0 474 190 A1 | 3/1992 | European Pat. Off. . |

OTHER PUBLICATIONS

Nitsch, R.M. et al., "Evidence for a membrane defect in Alzheimer disease brain," *Proc. Natl. Acad. Sci. USA* 89:1671–1675 (Mar. 1992).

Pettegrew, J.W. et al., "Correlation of Phosphorus–31 Magnetic Resonance Spectroscopy and Morphological Findings in Alzheimer's Disease," *Archives of Neurology* 45(10): 1093–1096 (1988).

Kwee, I.L. et al., "Elevation in relative levels of brain membrane unsaturated fatty acids in Alzheimer's disease: high resolution proton spectroscopic studies of membrane lipid extracts," *Magn. Reson. Med.* 21(1):49–54 (1991). (From Chemical Abstracts 116(19): Abstract No. 192004 (1992)).

Dyrks, T. et al., "Identification, transmembrane orientation and biogenesis of the amyloid A4 precursor of Alzheimer's disease," *EMBO J.* 7(4):949–957 (1988).

Blusztajn, Jan K., et al., "Abnormal Phospholipid Metabolism In Neurodegenerative Diseases: Elevations in Glycerophosphocholine and Glycerophosphoethanolamine Levels in Brain of Alzheimer's Disease but not in Down Syndrome Patients," Basic, Clinical, and Therapeutic Aspects of Alzheimer's and Parkinson's Diseases, (T. Nagatsu et al., etc., *Plenum Press*) I:133–138 (1990).

Skinner, E. Roy, et al., "Lipid Composition of Different Regions of the Brain in Patients with Alzheimer's Disease," *Biochemical Society Transactions* 17(1):213–214 (1988).

(List continued on next page.)

*Primary Examiner*—Nina Bhat
*Attorney, Agent, or Firm*—Lowe, Price, LeBlanc & Becker

[57] ABSTRACT

An antemortem diagnostic test for neurodegenerative disease, particularly Alzheimer's disease, is disclosed. The method of the invention involves the collection of a sample of bodily fluid; the analysis of the concentration of neuronal membrane phospholipids and phospholipid metabolites, or the ratio of a phospholipid to its metabolite, in the sample; and the correlation of the concentration or the ratio to the corresponding value from control samples. The method can be used to determine the presence or the possibility that an individual can develop a neurodegenerative disease, such as Alzheimer's disease; to follow the course of neurodegenerative disease in an individual; and to validate the efficacy of a drug used to treat a neurodegenerative disease.

15 Claims, 1 Drawing Sheet

OTHER PUBLICATIONS

Kawakatsu, Shinobu et al., "Acetylcholinesterase Activities and Monoamine Metabolite Levels in the Cerebrospinal Fluid of Patients with Alzheimer's Disease," *Biol. Psychiatry* 28: 387–400 (1990).

Bisso, G.M., et al., "Molecular Forms of Cholinesterases in CSF of Alzheimer's Disease/Senile Dementia of Alzheimer Type Patients and Matched Neurological Controls," *Life Sciences* 38:561–567 (1986).

Blusztajn, Jan K., et al., "Levels of Phospholipid Catabolic Intermediates, Glycerophosphocholine and Glycerophosphoethanolamine, Are Elevated in Brains of Alzheimer's Disease but not of Down's Syndrome Patients," *Brain Research* 536:240–244 (1990).

Söderberg, M., et al., "Lipid Composition in Different Regions of the Brain in Alzheimer's Disease/Senile Dementia of Alzheimer's Type," *Journal of Neurochemistry* 59:1646–1653 (1992).

Maire, Jean–Claude E., et al., "Choline Production from Choline–Containing Phospholipids: A Hypothetical Role in Alzheimer's Disease and Aging," *Prog. NeuroPsychopharmacol. & Biol. Psychiat.* 8:637–642 (1984).

Reinikainen, K. J., et al., "Cholinergic Deficit in Alzheimer's Disease: A Study Based on CSF and Autopsy Data," *Neurochemical Research* 13(2):135–146 (1988).

Wurtman, Richard J., et al., "Use of Choline in Cholinergic Neurons to Form Acetylcholine or Phosphatidylcholine: Implications for the Pathogenesis of Age–Related Memory Disorders," *Aging Brain and Dementia: New Trends in Diagnosis and Therapy* 54:215–258 (1990).

Elble, Rodger, et al., "Choline Levels are Increased in Cerebrospinal Fluid of Alzheimer Patients," *Neurobiology of Aging* 10:45–50 (1989).

Atack, John R., et al., "Cerebrospinal Fluid Cholinesterases in Aging and in Dementia of the Alzheimer Type," *Ann. Neurol.* 23:161–167 (1988).

Growdon, J.H. and M. Logue, "Choline, HVA, and 5–HIAA Levels in Cerebrospinal Fluid of Patients with Alzheimer's Disease," *Alzheimer's Disease: A Report of Progress* (Aging 19:35–43), edited by S. Corkin et al., Raven Press, New York (1982).

Blusztajn, J.K. et al., "The Possible Role of Neuronal Choline Metabolism in the Pathopsysiology of Alzheimer's Disease," *Adv. Basic Res. Ther. Proc. Meet. Int. Study Group Treat Mem. Disord. Assoc. Aging* 3rd:183–98 (1984).

Hollander et al, Neubiology of Aging, vol. 7, pp. 367–387 1986 "Antemortem Markers of AD".

Miller et al "Neurobiological Aging" vol. 12(1) pp. 61–64, 1991 Differences in Red Blood Cell . . . AD.

Nitsch et al, Annals of New York Academy of Science "Alterations of Phospholipid Metabolites . . . AD".

Blusztajn et al, Brain Research, "Levels of Phospholipid . . . Down's Syndrome Patients", 1990, pp. 240–244.

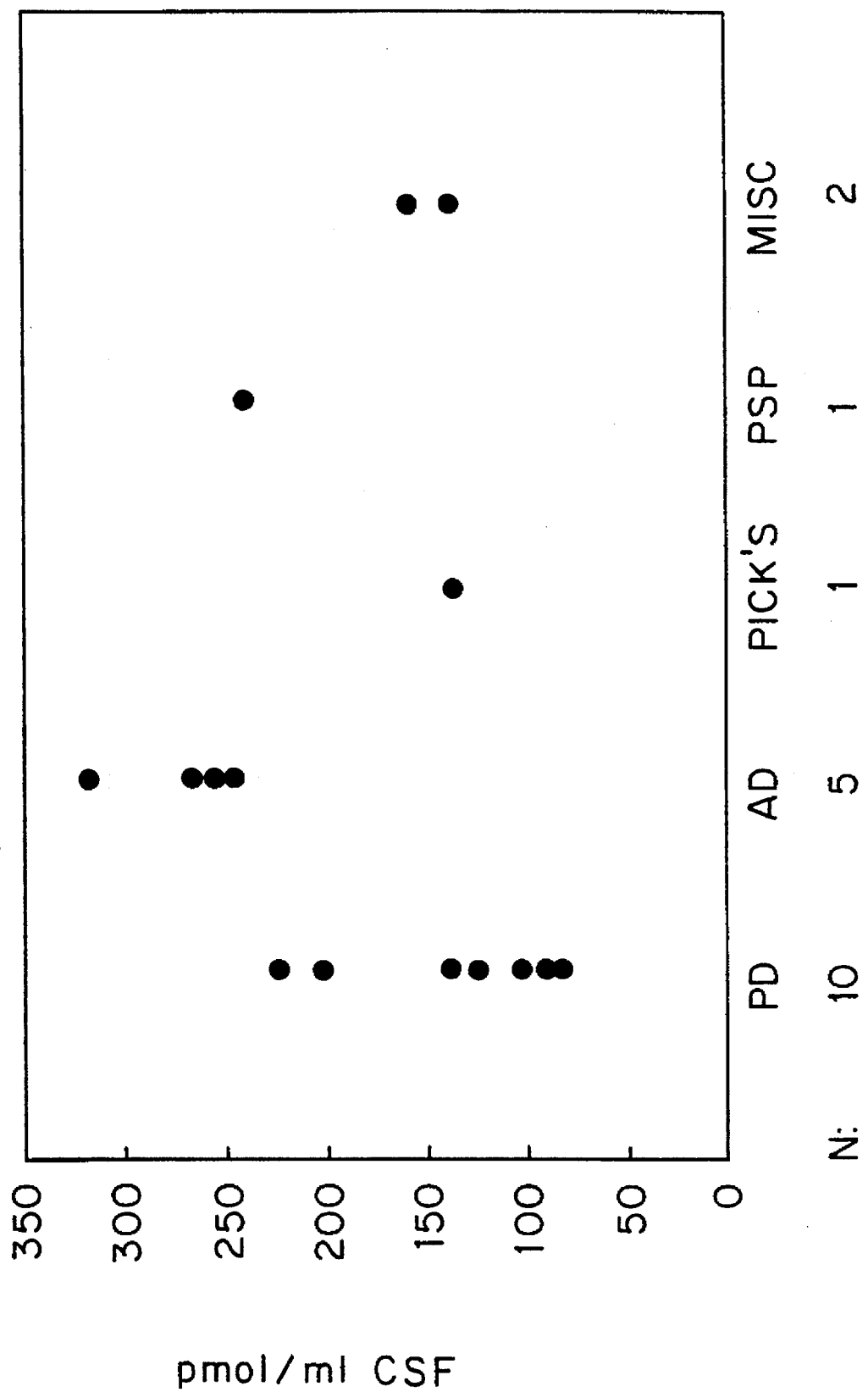

ANTEMORTEM DIAGNOSTIC TEST FOR ALZHEIMER'S DISEASE

DESCRIPTION

This application is a continuation of co-pending application Ser. No. 07/959,084 filed on Oct. 9, 1992, which is incorporated herein by reference in its entirety.

FUNDING

Work described herein was supported by the National Institutes of Health, the National Institute on Aging, and the Institute of Mental Health.

BACKGROUND

Alzheimer's disease (AD) is a chronic progressive neurodegenerative disease. Clinically, it is characterized by progressive deficits in memory and other cognitive functions that occur in the face of an otherwise normal neurological examination. Postmortem examination reveals a variety of typical AD brain lesions, including deposition of amyloid plaques, formation of neurofibrillary tangles, and neuronal degeneration. The etiology and pathophysiology of neuronal death are unknown.

Despite the fact that Alzheimer's disease is the most common neurological disease in the United States, there are no reliable antemortem biological tests for its diagnosis. Currently diagnosis rests on clinical grounds, and thus accuracy depends on the degree of physician expertise. An objective method for antemortem diagnosis of AD would be extremely useful: it would distinguish AD from other forms of dementia which may be curable; it would enable the patient to enter a treatment program early in the development of the disease, thus enhancing the opportunity for beneficial therapy; and it would allow patients in the early stages of the disease to plan for future nursing care, as well as to address other issues concerning the future needs of the patient's family.

SUMMARY OF THE INVENTION

This invention is based in the discovery that the presence of abnormalities in phospholipid metabolism in the brain can be identified by measuring levels of neuronal phospholipids and their metabolites in other tissues or in bodily fluids, such as cerebrospinal fluid (CSF), blood, or urine; and in the discovery that there is a relationship between these levels and neurodegenerative disease, particularly AD. The phospholipids and their metabolites are separated by known methods, such as HPLC and fractionation. When compared with standardized controls, altered levels of two of the most common phospholipids—phosphatidylcholine and phosphatidylethanolamine—and of their respective metabolites can be found. Certain changes, such as an elevated level of the phosphatidylcholine metabolite glycerophosphocholine (GPC), or an increased ratio of phosphatidylcholine to GPC, or of phosphatidylethanolamine to glycerophosphoethanolamine (GPE), indicate the presence of AD.

The present invention includes a method of diagnosing AD, and of assessing or detecting the presence of abnormalities which may exist before the clinical manifestations of the disease become evident and, thus, can be predictive of AD. The potential for effective treatment is greatest when commenced early in the progression of the disease, and, therefore, the present method is particularly useful because earlier diagnosis is now possible. Furthermore, the invention makes available a biological marker useful as an indicator of the effectiveness of treatments in altering or correcting abnormal neuronal metabolism.

BRIEF DESCRIPTION OF THE FIGURE

The FIGURE is a graphic representation CSF levels of GPC in several neurodegenerative diseases. Key: PD—Parkinson's Disease; AD—Alzheimer's Disease; PSP—Progressive Supranuclear Palsy; PICK'S—Pick's Disease.

DETAILED DESCRIPTION OF THE INVENTION

The present invention relates to a method of measuring the levels, in a bodily fluid, or in a sample of a tissue other than brain, of certain phospholipids and their metabolites whose presence within a range is known to be indicative of the occurrence of a neurodegenerative disease such as Alzheimer's Disease. It has been demonstrated that cell membrane lipid abnormalities contribute to the amyloid deposition and neuronal dysfunction of AD (Dyrks et al., *EMBO J.* 7, 949 (1988); Nitsch et al., *Neurology* 41 (Suppl. 1), 269 (abstr.) (1991); Pettegrew et al., *Arch. Neurol.* 45, 1093 (1988)). The current invention pertains to the discovery that it is possible to detect and quantify amounts of certain neuronal phospholipids and their metabolites in the bodily fluid of a human, such as cerebrospinal fluid (CSF), blood, and urine, and to correlate the levels to indicators of neurodegenerative disease, such as AD. Levels of phospholipids and phospholipid metabolites in samples of fluid from humans who do not currently demonstrate clinical manifestations of neurodegenerative disease are compared to the levels in samples from humans displaying neurodegenerative disease characteristics. Differences in amounts of certain phospholipids or their metabolites are then linked to particular diseases, such as AD.

As described in the Exemplification, Applicants have shown that a high level of the phosphatidylcholine metabolite GPC corresponds to the presence of AD, and not to the presence of other neurodegenerative diseases. As described, levels of GPC were measured in samples of CSF from individuals (humans) with Parkinson's Disease, Progressive Supranuclear Palsy, Pick's Disease, Alzheimer's Disease (AD), and other miscellaneous (nonspecified) diseases. The results, as shown in the Figure, indicated that the levels of GPC in the AD samples were higher than the levels in the other samples.

Samples obtained from three groups of individuals—individuals diagnosed with AD by presently available diagnostic methods (the AD-positive group); individuals diagnosed with a neurodegenerative disease other than AD (the neurodegenerative disease-positive, AD-negative group); and individuals who are not currently clinically presenting symptoms of any neurodegenerative disease (the neurodegenerative disease-negative group)—provide data concerning the ranges of concentrations and the ratios of phospholipids to phospholipid metabolites which are typically present in such individuals. Corresponding samples of bodily fluid, such as CSF, blood, and/or urine, are taken from individuals from each of the three groups. Samples from each control group are analyzed using known methods to determine the levels of neuronal phospholipids, such as phosphatidylcholine, phosphatidylethanolamine, and phosphatidylserine, and/or their metabolites, such as choline, GPC, ethanolamine and GPE; ratios of phospholipids and metabolites can also be calculated. The results from these groups provide control levels and control ratios to which other samples can be compared. After controls are established, samples can be taken from individuals with unknown disease status. The levels of phospholipids and their metabolites are quantified and compared to the controls. A significant variation from the controls indicates the presence of an abnormality in phospholipid metabolism indicative of neurodegenerative disease such as AD.

Although the method described results in quantification of the concentrations of phospholipids such as phosphatidylcholine and phosphatidylethanolamine, and phospholipid metabolites such as GPC and GPE, any other neuronal component for which a relationship can be shown can serve as a basis for the current method. Other bases for the current invention can be identified using the method described. The current method can also be used to identify the presence of other diseases, in addition to AD, in which a relationship between phospholipids or phospholipid metabolites and the occurrence of disease can be shown.

In addition, the current method can be used to follow the course of a neurodegenerative disease in an individual. Levels or ratios of phospholipids and phospholipid metabolites are taken from the individual in a series of correlating samples over a period of time, in order to monitor changes in the values. The values from these samples are compared to the control samples described above, to relate the values to those of other individuals with the disease, and thereby determine the severity of disease.

The method can also be used to assess the efficacy of a drug for the treatment of neurodegenerative disease. Levels or ratios of phospholipids and phospholipid metabolites in samples taken from an individual before the administration of the drug are compared to levels or ratios in a corresponding samples taken from the individual after administration of the drug. These values are further compared to those of the control samples described above. Efficacy of the drug is demonstrated if the levels or ratios after drug administration are closer to neurodegenerative-disease negative values than the levels or ratios before drug administration.

The invention will now be illustrated by the following Exemplification.

Exemplification: Comparison of Levels of Glycerophosphocholine in Cerebrospinal Fluid of Patients with Neurodegenerative Disease Protocol for Collection of Cerebrospinal Fluid Sample Before samples are obtained from an individual, a medical history is taken and a physical examination performed. The individual may take any usual medication, except for antidepressants, sedatives, hypnotics, or other agents which may affect brain function. The individual must lie flat from midnight until the time the sample is collected in the morning, and refrain from smoking, from taking a morning dosage of any usual medication, from eating, and from drinking any substance other than water during the same time period. A sample of cerebrospinal fluid is then collected using known methods.

Comparison of Samples

Cerebrospinal fluid samples were obtained from the Alzheimer's Disease Research Center at Massachusetts General Hospital. The specimens had been collected previously and had been stored at −70° C. until biochemical analysis. Initial experiments showed that GPC is stable over long periods of time (data not shown); thus, samples collected over a time period of years can easily be used for comparisons.

GPC levels in the CSF of five patients with clinically diagnosed probable Alzheimer's disease were compared to those of ten patients with Parkinson's disease; one Pick's disease patient, one patient with progressive supranuclear palsy, and two patients with miscellaneous diseases which were not further specified. Among those 19 samples, which were measured in a blind study, the five values which ranked highest were from the five AD patients. There was no overlap of the GPC values in the CSF of the five AD patients and the values from those patients with other diagnoses.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of screening for Alzheimer's disease in a human, comprising the steps of:
   a. determining the concentration of a neuronal phospholipid selected from the group consisting of phosphatidylcholine and phosphatidylethanolamine, or the concentration of a neuronal phospholipid metabolite selected from the group consisting of metabolites of phosphatidylcholine and metabolites of phosphatidylethanolamine, in a sample of cerebrospinal fluid obtained from the human, thereby obtaining a test value; and
   b. comparing the test value with a control value, wherein the control value is the concentration of the neuronal phospholipid or the neuronal phospholipid metabolite in a sample of cerebrospinal fluid from a human who does not currently demonstrate clinical manifestation of neurodegenerative disease, wherein a test value greater than the control value is indicative of Alzheimer's disease.

2. The method of claim 1, wherein the phospholipid metabolite is further selected from the group consisting of choline, glycerophosphocholine, ethanolamine, and glycerophosphoethanolamine.

3. A method of screening for Alzheimer's disease in a human, comprising the steps of:
   a. determining a ratio of the concentration of a neuronal membrane phospholipid to the concentration of its metabolite, the ratio selected from the group consisting of: the ratio of the concentration of phosphatidylcholine to the concentration of a phosphatidylcholine metabolite, or the ratio of the concentration of phosphatidylethanolamine to the concentration of a phosphatidylethanolamine metabolite, in a sample of cerebrospinal fluid obtained from the human, thereby obtaining a test ratio; and
   b. comparing the test ratio with a control ratio, wherein the control ratio is the same ratio determined in a) in a sample of cerebrospinal fluid from a human who does not currently demonstrate clinical manifestation of neurodegenerative disease, wherein a test ratio greater than the control ratio is indicative of Alzheimer's disease.

4. The method of claim 3, wherein the phospholipid metabolite is further selected from the group consisting of choline, glycerophosphocholine, ethanolamine, and glycerophosphoethanolamine.

5. A method of screening for Alzheimer's disease in a human, comprising the steps of:
   a. collecting a sample of cerebrospinal fluid from the human;
   b. determining a test value selected from the group consisting of:

(i) the concentration of a neuronal phospholipid selected from the group consisting of phosphatidylcholine and phosphatidylethanolamine;

(ii) the concentration of a neuronal phospholipid metabolite selected from the group consisting of metabolites of phosphatidylcholine and metabolites of phosphatidylethanolamine; and (iii) a ratio of the concentration of a neuronal membrane phospholipid to the concentration of its metabolite, the ratio being selected from the group consisting of: the ratio of the concentration of phosphatidylcholine to the concentration of a phosphatidylcholine metabolite, or the ratio of the concentration of phosphatidylethanolamine to the concentration of a phosphatidylethanolamine metabolite in the sample; and c. comparing the test value with a control value, wherein the control value is the same concentration or ratio determined in b) in a sample of cerebrospinal fluid from a human who does not currently demonstrate clinical manifestation of neurodegenerative disease, wherein a test value greater than the control value is indicative of Alzheimer's disease.

6. The method of claim 5, wherein the phospholipid metabolite is further selected from the group consisting of choline, glycerophosphocholine, ethanolamine, and glycerophosphoethanolamine.

7. A method of predicting the likelihood that a human will develop Alzheimer's disease, comprising the steps of:

a. collecting a sample of cerebrospinal fluid from the human;

b. determining a test value selected from the group consisting of:

(i) the concentration of a neuronal phospholipid selected from the group consisting of phosphatidylcholine and phosphatidylethanolamine;

(ii) the concentration of a neuronal phospholipid metabolite selected from the group consisting of metabolites of phosphatidylcholine and metabolites of phosphatidylethanolamine; or (iii) a ratio of the concentration of a neuronal membrane phospholipid to the concentration of its metabolite, the ratio being selected from the group consisting of: the ratio of the concentration of phosphatidylcholine to the concentration of a phosphatidylcholine metabolite, or the ratio of the concentration of phosphatidylethanolamine to the concentration of a phosphatidylethanolamine metabolite in the sample; and c. comparing the test value with a control value, wherein the control value is the same concentration or ratio determined in b) in a sample of cerebrospinal fluid from a human who does not currently demonstrate clinical manifestation of neurodegenerative disease, wherein a test value greater than the control value is indicative of the likelihood of development of Alzheimer's disease.

8. The method of claim 7, wherein the phospholipid metabolite is further selected from the group consisting of choline, glycerophosphocholine, ethanolamine, and glycerophosphoethanolamine.

9. A method of following the course of Alzheimer's disease in a human, comprising the steps of:

a. determining the concentration of a neuronal phospholipid selected from the group consisting of phosphatidylcholine and phosphatidylethanolamine, or the concentration of a neuronal phospholipid metabolite selected from the group consisting of metabolites of phosphatidylcholine and metabolites of phosphatidylethanolamine, in a series of correlating samples of cerebrospinal fluids taken from the human at regular intervals after diagnosis of probable Alzheimer's disease, thereby obtaining a series of test values; and b. comparing the test values with a control value, wherein the control value is the concentration of the neuronal phospholipid or the neuronal phospholipid in a sample of cerebrospinal fluid from a human who does not currently demonstrate clinical manifestation of neurodegenerative disease, wherein an increase in the deviation of the concentration of a first test value from the control value, as compared with the deviation of the concentration of a second test value from the subsequent interval from the control value, is indicative of progression of Alzheimer's disease.

10. The method of claim 9, wherein the phospholipid metabolite is further selected form the group consisting of choline, glycerophosphocholine, ethanolamine, and glycerophosphoethanolamine.

11. A method of following the course of Alzheimer's disease in a human, comprising the steps of:

a. determining the ratio of the concentration of a neuronal membrane phospholipid to the concentration of its metabolite, the ratio selected from the group consisting of: the ratio of the concentration of phosphatidylcholine to the concentration of a phosphatidylcholine metabolite, and the ratio of the concentration of phosphatidylethanolamine to a phosphatidylethanolamine metabolite, in a series of correlating samples of cerebrospinal fluids taken from the human at regular intervals after diagnosis of probable Alzheimer's disease, thereby obtaining a series of test ratio values, and b. comparing the test ratio values with a control ratio, wherein the control ratio is the same ratio determined in a) in a sample of cerebrospinal fluid from a human who does not currently demonstrate clinical manifestation of neurodegenerative disease, wherein an increase in the deviation of a first test ratio value from the control ratio value, as compared with the deviation of a second test ratio value from the subsequent interval from the control ratio value, is indicative of progression of Alzheimer's disease.

12. The method of claim 11, wherein the phospholipid metabolite is further selected from the group consisting of choline, glycerophosphocholine, ethanolamine, and glycerophosphoethanolamine.

13. A method of screening for Alzheimer's disease in a human, comprising the steps of:

a. determining the concentration of glycerophosphocholine in a sample of cerebrospinal fluid obtained from the human, thereby obtaining a test value; and b. comparing the test value with a control value, wherein the control value is the concentration of glycerophosphocholine from a sample of cerebrospinal fluid from a human who does not currently demonstrate clinical manifestation of neurodegenerative disease, wherein a test value greater than the control value is indicative of Alzheimer's disease.

14. A method of diagnosing Alzheimer's disease in a human, comprising the steps of:

a. determining the ratio of the concentration of phosphatidylcholine to the concentration of glycerophosphocholine in a sample of cerebrospinal fluid obtained from the human, thereby obtaining a test ratio; and b. comparing the test ratio with a control ratio, wherein the control ratio is the ratio of the concentration of phosphatidylcholine to the concentration of glycerophosphocholine from a sample of cerebrospinal fluid from a human who does not currently demonstrate clinical manifestation of neurodegenerative disease, wherein a test ratio greater than the control ratio is indicative of Alzheimer's disease.

15. A method of diagnosing Alzheimer's disease in a human, comprising the steps of:

a. collecting a sample of cerebrospinal fluid from the human;

b. determining a test value selected from the group consisting of: the concentration of glycerophosphocholine, and the ratio of phosphatidylcholine to glycerophosphocholine in the sample; and c. comparing the test value with a control value, wherein the control value is the corresponding test value from a sample of cerebrospinal fluid from a human who does not currently demonstrate clinical manifestation of disease, wherein a test value greater than the control value is indicative of Alzheimer's disease.

* * * * *